United States Patent
Raksi (10) Patent No.: US 8,939,967 B2
(45) Date of Patent: Jan. 27, 2015

(54) PATIENT INTERFACE DEFOGGER

(75) Inventor: Ferenc Raksi, Mission Viejo, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 472 days.

(21) Appl. No.: 13/197,071

(22) Filed: Aug. 3, 2011

(65) Prior Publication Data

US 2013/0035672 A1    Feb. 7, 2013

(51) Int. Cl.
*A61B 18/18*    (2006.01)
*A61F 9/009*    (2006.01)
*A61F 9/008*    (2006.01)

(52) U.S. Cl.
CPC .............. *A61F 9/009* (2013.01); *A61F 9/00825* (2013.01); *A61F 2009/00846* (2013.01); *A61F 2009/00851* (2013.01)
USPC .................................................. 606/10; 606/4

(58) Field of Classification Search
CPC ................... A61B 2017/306; A61B 2017/308; A61B 9/00; A61B 9/0009; A61B 9/0061; A61B 2009/008; A61B 2009/0087
USPC ....................... 414/751.1, 751.2, 751.3, 749.6
See application file for complete search history.

(56) References Cited

U.S. PATENT DOCUMENTS

| | | |
|---|---|---|
| 3,706,304 A | 12/1972 | Sisler |
| 4,367,018 A | 1/1983 | Abe |
| 4,453,546 A | 6/1984 | Katz et al. |
| 4,600,008 A | 7/1986 | Schmidt |
| 4,718,418 A | 1/1988 | L'Esperance, Jr. |
| 4,753,526 A | 6/1988 | Koester |
| 4,905,711 A | 3/1990 | Bennett et al. |
| 4,907,586 A | 3/1990 | Bille et al. |
| 4,964,717 A | 10/1990 | Koester |
| 4,994,058 A | 2/1991 | Raven et al. |
| 5,108,412 A | 4/1992 | Krumeich et al. |
| 5,112,328 A | 5/1992 | Taboada et al. |
| 5,128,509 A | 7/1992 | Taboada et al. |
| 5,196,027 A | 3/1993 | Thompson et al. |
| 5,226,903 A | 7/1993 | Mizuno |
| 5,252,998 A | 10/1993 | Reis et al. |
| 5,280,491 A | 1/1994 | Lai |
| 5,311,224 A | 5/1994 | Enomoto |
| 5,324,281 A | 6/1994 | Muller |

(Continued)

FOREIGN PATENT DOCUMENTS

| | | |
|---|---|---|
| CA | 2128104 A1 | 7/1993 |
| EP | 0627207 | 12/1994 |

(Continued)

OTHER PUBLICATIONS

International Search Report dated Sep. 5, 2012 for corresponding International Application No. PCT/US2012/036546, 3 pages.

(Continued)

*Primary Examiner* — Ahmed Farah (57) ABSTRACT

An ophthalmic docking system is presented that can reduce a condensation of a patient interface of a surgical laser system. The ophthalmic docking system includes a patient interface that has a proximal portion configured to be attached to an ophthalmic system, a distal portion configured to be attached to an eye that includes a contact lens and an interface attachment system; and a decondenser, coupled to the patient interface and configured to reduce a vapor condensation on the contact lens.

14 Claims, 13 Drawing Sheets

(56) References Cited

U.S. PATENT DOCUMENTS

| | | | |
|---|---|---|---|
| 5,336,215 | A | 8/1994 | Hsueh et al. |
| 5,360,424 | A | 11/1994 | Klopotek |
| 5,364,390 | A | 11/1994 | Taboada et al. |
| 5,423,801 | A | 6/1995 | Marshall et al. |
| 5,450,144 | A | 9/1995 | Ben Nun |
| 5,549,632 | A | 8/1996 | Lai |
| 5,656,186 | A | 8/1997 | Mourou et al. |
| 5,861,955 | A | 1/1999 | Gordon |
| 5,871,772 | A | 2/1999 | Cantoro |
| 5,957,832 | A | 9/1999 | Taylor et al. |
| 6,019,472 | A | 2/2000 | Koester et al. |
| 6,090,100 | A | 7/2000 | Hohla |
| 6,143,010 | A | 11/2000 | Silvestrini et al. |
| 6,210,401 | B1 | 4/2001 | Lai |
| 6,254,595 | B1 | 7/2001 | Juhasz et al. |
| 6,342,053 | B1 | 1/2002 | Berry |
| 6,344,040 | B1 | 2/2002 | Juhasz et al. |
| 6,373,571 | B1 | 4/2002 | Juhasz et al. |
| 6,412,334 | B1 | 7/2002 | Kral et al. |
| 6,436,113 | B1 | 8/2002 | Burba et al. |
| 6,451,006 | B1 | 9/2002 | Bille |
| 6,458,141 | B1 | 10/2002 | Peyman |
| 6,579,282 | B2 | 6/2003 | Bille et al. |
| 6,623,476 | B2 | 9/2003 | Juhasz et al. |
| 6,634,753 | B1 | 10/2003 | Rozenman |
| 6,641,577 | B2 | 11/2003 | Bille |
| 6,676,653 | B2 | 1/2004 | Juhasz et al. |
| 6,730,073 | B2 | 5/2004 | Bruce |
| 6,730,074 | B2 | 5/2004 | Bille et al. |
| 6,733,491 | B2 | 5/2004 | Kadziauskas et al. |
| 6,752,778 | B1 | 6/2004 | Fiedler et al. |
| 6,776,824 | B2 | 8/2004 | Wen |
| 6,780,176 | B2 | 8/2004 | Hasegawa |
| 6,863,667 | B2 | 3/2005 | Webb et al. |
| 6,899,707 | B2 | 5/2005 | Scholler et al. |
| 6,905,641 | B2 | 6/2005 | Platt et al. |
| 6,991,629 | B1 | 1/2006 | Juhasz et al. |
| 7,018,376 | B2 | 3/2006 | Webb et al. |
| 7,125,119 | B2 | 10/2006 | Farberov |
| 7,238,176 | B2 | 7/2007 | Loesel et al. |
| 7,244,026 | B1 | 7/2007 | Ross, III et al. |
| 7,285,096 | B2 | 10/2007 | Burba et al. |
| 7,330,275 | B2 | 2/2008 | Raksi |
| 7,371,230 | B2 | 5/2008 | Webb et al. |
| 7,390,089 | B2 | 6/2008 | Loesel et al. |
| 7,402,159 | B2 | 7/2008 | Loesel et al. |
| 7,452,080 | B2 | 11/2008 | Wiltberger et al. |
| 7,452,081 | B2 | 11/2008 | Wiltberger et al. |
| 7,611,507 | B2 | 11/2009 | Raksi et al. |
| 8,070,290 | B2 | 12/2011 | Gille et al. |
| 2001/0021844 | A1 | 9/2001 | Kurtz et al. |
| 2002/0103481 | A1 | 8/2002 | Webb et al. |
| 2002/0103482 | A1 | 8/2002 | Scholler et al. |
| 2003/0153904 | A1 | 8/2003 | Patel |
| 2004/0070761 | A1 | 4/2004 | Horvath et al. |
| 2004/0254568 | A1 | 12/2004 | Rathjen |
| 2005/0143718 | A1 | 6/2005 | Rathjen |
| 2005/0154408 | A1 | 7/2005 | Dybbs |
| 2006/0179992 | A1 | 8/2006 | Kermani |
| 2006/0195078 | A1 | 8/2006 | Webb et al. |
| 2006/0261502 | A1 | 11/2006 | Platt et al. |
| 2007/0093795 | A1 | 4/2007 | Melcher et al. |
| 2007/0093796 | A1 | 4/2007 | Raksi et al. |
| 2007/0173791 | A1 | 7/2007 | Raksi |
| 2007/0253083 | A1 | 11/2007 | Muhlhoff et al. |
| 2008/0071254 | A1* | 3/2008 | Lummis et al. ............ 606/4 |
| 2008/0194915 | A1 | 8/2008 | Blackhurst et al. |
| 2009/0069794 | A1 | 3/2009 | Kurtz |
| 2009/0137989 | A1 | 5/2009 | Kataoka |
| 2009/0182310 | A1 | 7/2009 | Gertner et al. |
| 2011/0166535 | A1 | 7/2011 | Hasegawa et al. |
| 2011/0190739 | A1 | 8/2011 | Frey et al. |
| 2011/0319873 | A1 | 12/2011 | Raksi et al. |

FOREIGN PATENT DOCUMENTS

| | | |
|---|---|---|
| EP | 0536951 B1 | 8/1997 |
| EP | 0634947 B1 | 12/2001 |
| EP | 1982640 | 10/2008 |
| WO | 8803396 A1 | 5/1988 |
| WO | 8906519 A2 | 7/1989 |
| WO | 2011163507 A2 | 12/2011 |

OTHER PUBLICATIONS

International Search Report dated Feb. 29, 2012 for corresponding International Application No. PCT/US2011/041676, 3 pages.

European Supplementary Search Report for European Application No. 087994331 with mailing date Feb. 13, 2013, 6 pages.

International Search Report for corresponding International Application No. PCT/US2012/049319 with mailing date Nov. 19, 2012, 4 pages.

International Search Report for corresponding International Application No. PCT/US2012/052460 with mailing date Dec. 11, 2012, 6 pages.

Chinn, S. R., et al., Optical coherence tomography using a frequency-tunable optical source, Optics Letters, Mar. 1, 1997, pp. 340-342, vol. 22, No. 5.

Huber, R., et al, Three-dimensional and C-mode OCT imaging with a compact, frequency swept laser source at 1300 nm, Optics Express, Dec. 26, 2005, pp. 10523-15038, vol. 13, No. 26.

International Search Report and Written Opinion dated Mar. 19, 2009 for International Application No. PCT/US2008/075902, filed Sep. 10, 2008, 8 pages.

Yun, S. H., et al., Wavelength-Swept Fiber Laser with Frequency Shifted Feedback and Resonantly Swept Intra-Cavity Acoustooptic Tunable Filter, IEEE Journal of Selected Topics in Quantum Electronics, Aug. 1997, pp. 1087-1096, vol. 3, No. 4.

* cited by examiner

PATIENT INTERFACE DEFOGGER

TECHNICAL FIELD

This patent document relates to patient interfaces for ophthalmic procedures. In more detail, this patent document relates to defogging systems for patient interfaces of ophthalmic surgical laser systems.

BACKGROUND

The widespread introduction and acceptance of laser surgical systems in ophthalmic applications ushered in a new era of precision and control. One of the keys to achieving this high level of control is the immobilization of the eye relative to the laser surgical system. In many devices the immobilization is carried out by affixing a patient interface to the objective of the laser surgical system and then docking the patient interface onto the eye. The docking is often achieved by engaging a vacuum suction system. To provide a well-defined optical interface with a known curvature for the optic and the laser beam of the laser surgical system, patient interfaces typically include a contact lens or applanation lens that makes direct contact with the cornea of the imaged eye.

One of the factors the precision and utility of these systems depends on is the patient interface being docked to the eye in a central position. Such a central docking, or centering, aligns an optical axis of the objective of the laser system and an optical axis of the eye. Since the surgical laser beam is typically directed and controlled relative to the optical axis of the objective, aligning the optical axis of the eye with the optical axis of the objective by a central docking can enable controlling and directing the laser beam in the eye with high precision.

Achieving a central docking is often a challenge, though, for multiple reasons. First, the surgical equipment can make maneuvering the objective cumbersome. Also, for some procedures, hard-to-see and hard-to-image structures of the eye, such as their lens, needs to be aligned with the patient interface. Since the lens is often not aligned with the visible structures of the eye, therefore centering the patient interface with a visible structure may result in a misalignment of the patient interface with the lens. Further, the patients sometimes move their eyes during docking, even against their own will, and these involuntary movements need to be compensated by adjusting the patient interface.

To achieve high precision during the alignment and the subsequent docking in face of these difficulties, laser surgical systems often assist the surgeon by including an advanced imaging system. This advanced imaging system can include a stereo microscope, a video monitor and sometimes an Optical Coherence Tomographic (OCT) device. However, integrating these advanced imaging systems into the surgical systems that also use a patient interface can introduce challenges for the system design.

SUMMARY

One of the design challenges is that during the alignment process the patient interface is kept a few millimeters above the eye for an extended period. During this time the surgeon can operate the video or OCT imaging systems, analyze the pictures and maneuver and adjust the objective by operating a gantry of the laser surgical system, for example. During all this time, however, water evaporates from the surface of the eye, creating a water vapor-rich atmosphere between the eye and the contact lens. In most systems, the temperature of the contact lens is typically lower than that of the body and the eye. Because of this temperature difference, the water can condense from the vapor onto the contact lens. This condensation can degrade the visibility through the patient interface, introducing blurriness to the video image and noise into the OCT image. Both these effects can disadvantageously reduce the precision of the alignment and docking process.

In this context, embodiments described in this patent document offer solutions for the problem of the condensation on the contact lens of the patient interface. In some embodiments, an ophthalmic docking system includes a patient interface, having a proximal portion configured to be attached to an ophthalmic system, a distal portion configured to be attached to an eye, including a contact lens and an interface attachment system, and a decondenser, coupled to the patient interface configured to reduce a vapor condensation on the contact lens.

In some embodiments, a method of ophthalmic docking includes providing a patient interface having a contact lens and coupled to a decondenser, generating a decondensing gas flow by the decondenser towards the contact lens prior to a docking of the patient interface to an eye, and docking the patient interface to the eye.

In some embodiments, an ophthalmic interface system includes a patient interface, attachable to an ophthalmic laser system, the patient interface including a contact lens to be docked to an eye, and a desiccating system, configured to direct a desiccating gas flow towards the contact lens.

DETAILED DESCRIPTION

Implementations and embodiments in this patent document provide an ophthalmic docking system that can reduce or eliminate the condensation on the contact lens of the patient interface.

Figure 1:
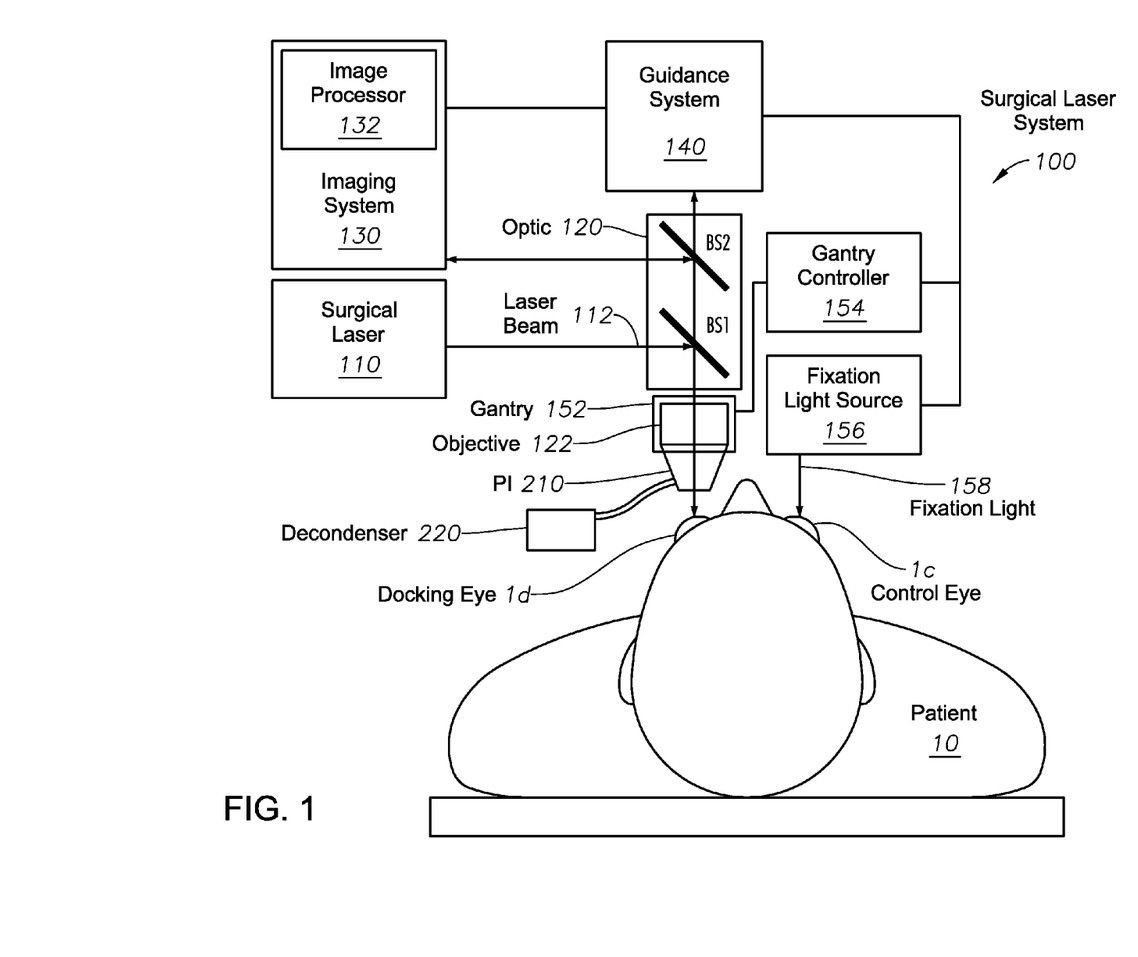
FIG. 1 illustrates an ophthalmic laser surgical system.

FIG. 1 illustrates an ophthalmic surgical laser system 100. The laser system 100 can include a surgical laser 110 that can generate and couple a surgical laser beam into an optic 120 at a beam splitter BS1. The surgical laser 110 can be capable of generating a pulsed laser beam with a femtosecond pulse length. The optic 120 can redirect and deliver the pulsed laser beam into a docking eye 1*d* of a patient 10 through an objective 122 and a patient interface, or PI, 210 that is docked onto the docking eye 1*d*.

The laser system 100 can also include an imaging system 130. The imaging system 130 can provide one or more images for an ophthalmic surgeon to increase the precision of the docking of the PI 210 and in general of the ophthalmic procedures carried out with the laser system 100. The images can include a stereoscopic microscope image, a video-image, and an Optical Coherence Tomographic, or OCT image. The image can be analyzed by an image processor 132.

The generated image can be displayed on a guidance system 140. One of the functions of the guidance system 140 can be to guide the surgeon to align a center of the eye and a center or axis of the optic 120 for optimizing the docking of the PI 210. In some embodiments, the guidance system 140 can include a video-monitor to display the video-image created by the imaging system 130. In other embodiments, the guidance system 140 can include an OCT display to display the OCT image created by the imaging system 130. In addition, the guidance system 140 can include a guidance display to guide the surgeon based on the result of the processing of the image by the image processor 132.

For example, the guidance display of the guidance system 140 can include a target pattern or a crosshair pattern overlaid on the video image of the eye to indicate a position of an optical center or axis of the optic 120 relative to a center of the eye. In other systems, the guidance system 140 can display one or more arrows to suggest the surgeon a corrective action to align the optic 120 and the eye 1d. In yet other systems, the guidance system 140 can display aligning icons determined from an analysis of the OCT image by the image processor 132.

The correction of the alignment can be initiated either by the surgeon or by a processor of the surgical laser system 100, in response to the above described types of guidance information generated by the guidance system 140. For example, some embodiments of the laser system 100 can include a gantry 152 and a gantry controller 154 to move the objective 122 laterally and align it with a center of the eye as part of the docking procedure. Such a gantry 152 can compensate a lateral or transverse misalignment of the eye 1d and the optic 120, but not necessarily a rotational misalignment.

A rotational or angular misalignment of the eye 1d and the optical axis of the optic 120 can be compensated by a fixation light source 156 that projects a fixation light 158 into a control eye 1c, for example. The patient 10 can be instructed to follow the movement of the fixation light 158. As the surgeon adjusts the fixation light 158, he or she can track the movement of the eye's video image relative to the optical axis of the optic 120 on the guidance display 140 and continue to adjust the fixation light 158 until the docking eye 1d is aligned with the optical axis of the optic 120 to the desired degree.

As described above, in the late stages of docking process including the alignment phase, the patient interface 210 may be only millimeters above the docking eye 1d. The wet surface of the docking eye 1d is continuously evaporating water vapor that can condense on a contact lens of the patient interface 210, since the temperature of the contact lens is typically lower than the body temperature and the vapor-rich air is getting trapped between the eye and the contact lens. This water condensate can fog up the optical pathway, making the video image blurry and the OCT image noisy. Therefore, the water condensation can undermine and endanger the precision and efficiency of the above alignment and docking process, threatening the success of the overall surgical procedure.

Figure 2:
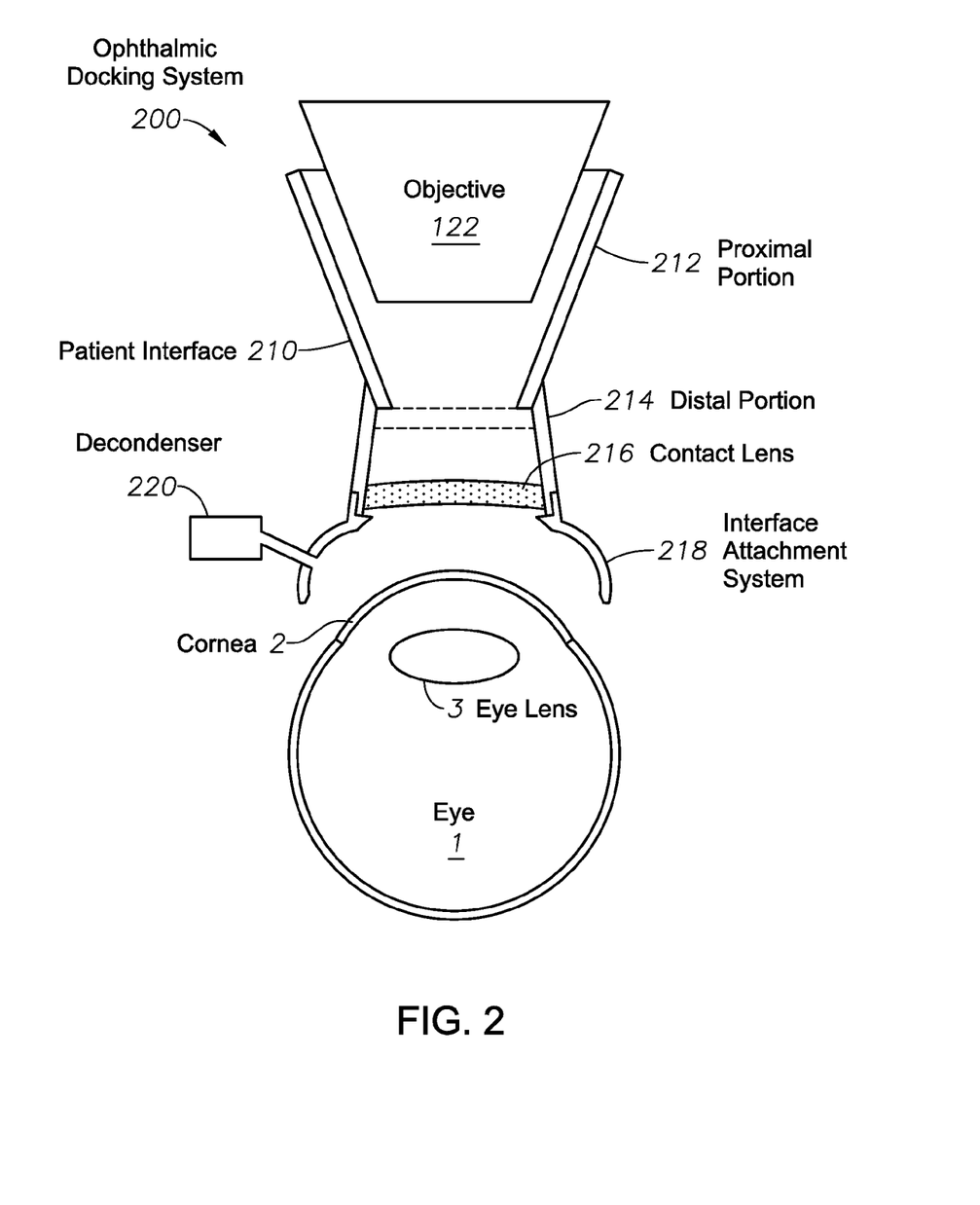
FIG. 2. illustrates an ophthalmic docking system with a decondenser.

FIG. 2 illustrates an embodiment of an ophthalmic docking system 200 that can offer solutions for the condensation problem. The docking system 200 can include the patient interface, or PI 210. The patient interface 210 can have a proximal portion or attachment cone 212, to be attached to an ophthalmic system, such as the surgical laser system 100 and in particular to its objective 122. The patient interface 210 can also include a distal portion 214 to be attached to an eye 1, such as the docking eye 1d.

In the embodiment of FIG. 2, the proximal portion 212 and the distal portion 214 can be integral parts of a single patient interface 210, which can be made of a single plastic mold or an elastic material, for example. In other embodiments, the portions 212 and 214 can be manufactured separately and then assembled during the manufacturing process. In yet other, later described embodiments, portions 212 and 214 can be separate elements that are affixed together by the surgeon during the docking process.

The distal portion 214 can include a contact lens or applanation lens 216 that is pressed against a cornea 2 of the eye 1 during docking to establish a well-defined and controlled optical interface between the optic 120 of the laser system 100 and the docking eye 1d or 1 for short. The well defined optical interface, defined by the contact lens 216 having e.g. a known radius of curvature, allows the high precision targeting of the surgical laser beam onto or into surgical targets, such as a lens 3 of the eye.

The distal portion 214 can also include an interface attachment system 218 as described below in detail. Further, the ophthalmic docking system 200 can include a decondenser 220. Some embodiments of the decondenser 220 can be called a defogger, a desiccator or a dehumidifier as well. The decondenser 220 can be coupled to the patient interface 210. One of the functions of the decondenser 220 can be to reduce a vapor condensation on the contact lens 216. This functionality can be achieved in different manners.

Figure 3A:
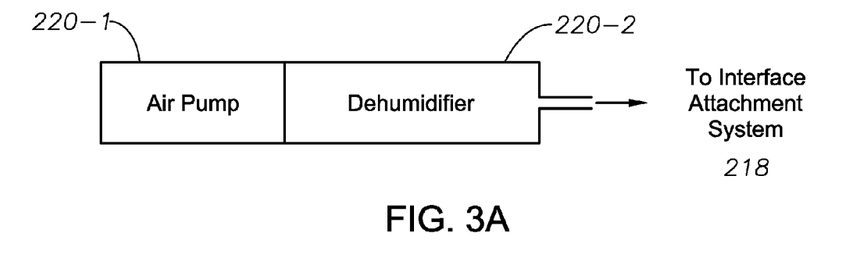
FIGS. 3A-E illustrate various embodiments of a decondenser.

FIG. 3A illustrates that some embodiments of the decondenser 220 deliver a suitably prepared airflow to the contact lens 216 to reduce the vapor condensation on the contact lens 216. Such decondensers 220 may include an air pump 220-1 that can pump air towards the interface attachment system 218. In its simplest realization, pumping ambient air by the air-pump 220-1 to the contact lens 216 can blow away the vapor-rich air between the contact lens 216 and the eye 1 and replace it with ambient air that does not contain excess vapor, thereby reducing the condensation on the contact lens 216.

Other decondensers 220 can include a dehumidifier or desiccator 220-2 that can reduce a vapor content of an airflow directed towards the interface attachment system 218 by the air pump 220-1. Once a reduced-vapor content air replaces the high-vapor content air evaporating from the eye 1, the fogging of the contact lens 216 is reduced or possibly eliminated. Here and later, embodiments can include their constituent elements in different order. For example, in some systems, the air pump 220-1 can pump the air into the dehumidifier 220-2, whereas in other systems the dehumidifier 220-2 can provide low-humidity air for the air pump 220-1.

Figure 3B:
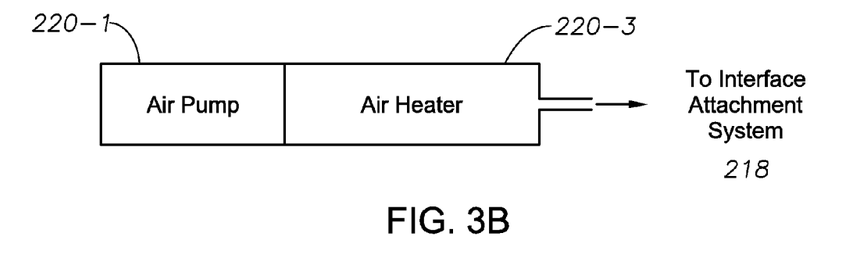

FIG. 3B illustrates that in some embodiments, the decondenser 220 can include an air-heater 220-3 that can increase a temperature of an airflow directed towards the interface attachment system 218. Heated air can defog the contact lens 216 by multiple mechanisms. Higher temperature air has a higher dew-point than ambient temperature air and therefore can accommodate more vapor without forcing its condensation into a dew or condensation on the contact lens 216. Thus, replacing the vapor-rich, ambient temperature air with higher temperature air reduces the condensation on the contact lens 216. Moreover, the heated air heats the contact lens 216 as well. For similar physical reasons as above, the warmer the contact lens 216, the lesser the degree of vapor condensation.

The air-heater 220-3 can include a temperature controller that controls the temperature of the heated air to approximately body temperature or slightly higher. A much higher temperature can cause irritation or burning of the corneal tissue, whereas a lower temperature may not be able to prevent the condensation effectively.

Figure 3C:
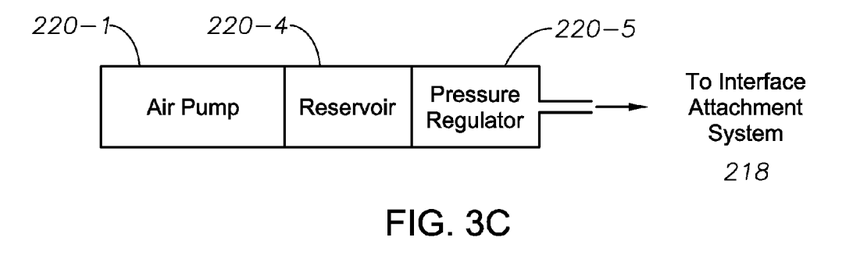

FIG. 3C illustrates that some decondensers 220 can include a reservoir 220-4 that can store high-pressure air pumped by the air pump 220-1 at a pressure higher than an ambient pressure. The reservoir 220-4 can be capable of forwarding the higher-than-ambient pressure, or high-pressure air towards the interface attachment system 218. Both the high pressure and the speed of the air reduce the condensation on the contact lens 216. The term high-pressure air can refer to air with a pressure higher than an ambient pressure. The pressure of the high-pressure air can be only moderately or fractionally higher than the ambient pressure.

A utility of the reservoir 220-4 is that a docking system 200 with a reservoir 220-4 can make use of a smaller air pump 220-1 that pumps up the reservoir 220-4 over an extended period to a pressure higher than what the air pump 220-1 could achieve in real time. In some sense, the reservoir 220-4 can advantageously "step-up", "up-convert", or "buffer" the pressure of the airflow.

In some embodiments, the pressure of the high-pressure air can be regulated by a pressure regulator 220-5. This pressure regulator 220-5 can be useful in systems where the air-pump 220-1 delivers the air with a varying pressure. The pressure can vary for different reasons. Most pumps operate by repeating a mechanical cycle with a high repetition rate. The pressure of the pumped air can oscillate within each cycle. Moreover, the operating voltage of the air pump 220-1 can drift or change when other sub-systems of the surgical laser system 100 start drawing power from the on-board power supply, or if the external voltage of the system 100 experiences a fluctuation.

If the pressure and thus speed of the air pumped from the decondenser 220 to the contact lens 216 fluctuates for any of the above reasons, it may have unwanted or undesirable impacts on the degree of the condensation on the contact lens 216. To compensate these pressure fluctuations, some embodiments of the decondenser 220 can include the pressure regulator 220-5 that can forward the high-pressure air towards the interface attachment system 218 with a pressure fluctuation smaller than a pressure fluctuation of the high-pressure air pumped by the air pump 220-1 to the reservoir 220-4. In some embodiments, the pressure regulator 220-5 can minimize or even eliminate the pressure fluctuations of the pumped air, received from the air pump 220-1.

Figure 3D:
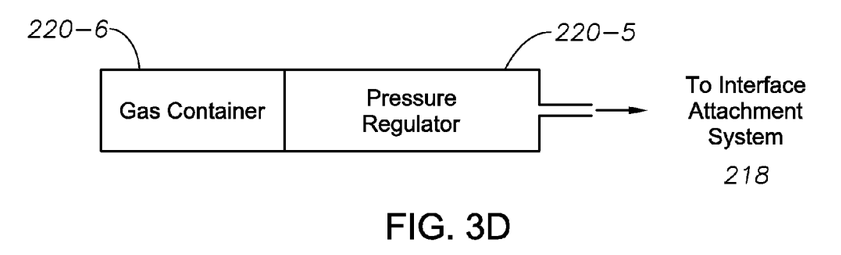

FIG. 3D illustrates that in some embodiments, the decondenser 220 can include a gas container 220-6 that can store a high-pressure gas at a pressure higher than an ambient pressure, and can forward this high-pressure gas towards the interface attachment system 218. The stored gas need not be air: it can be, for example, an inert gas or nitrogen, among others. Such systems can also include the pressure regulator 220-5 to regulate the pressure of the gas, as the gas container 220-6 may release the gas with a pressure that changes over time.

Figure 3E:
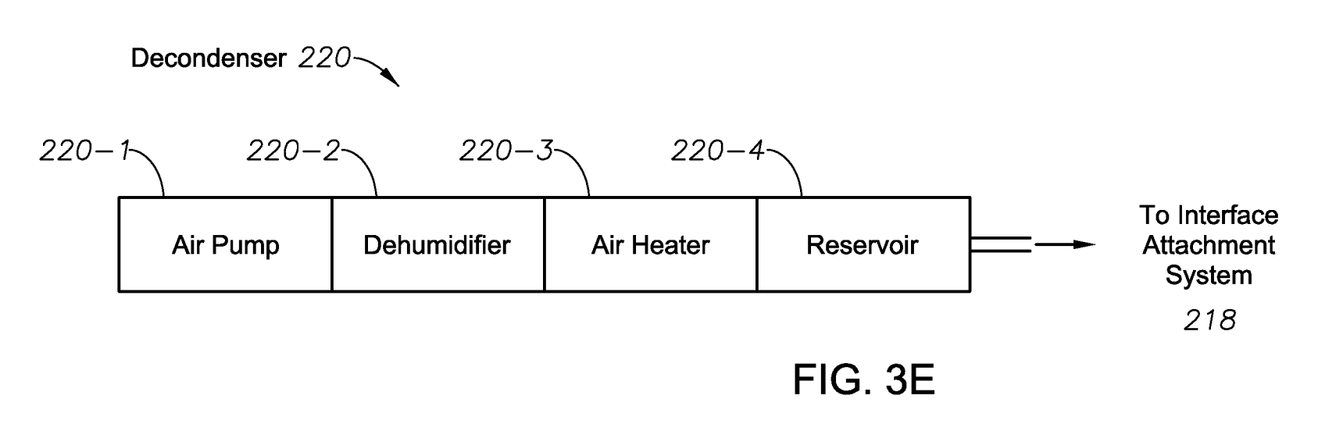

FIG. 3E illustrates that the elements of FIGS. 3A-D can be combined in different ways and in different sequences. For example, the decondenser or desiccator 220 of FIG. 3E can include the air-pump 220-1, pumping air to the dehumidifier 220-2, which can output a low-humidity airflow to the air-heater 220-3. The air-heater 220-3 can increase the temperature of this low-humidity airflow and guide it into the reservoir 220-4 that can buffer the airflow thus increasing the pressure of the stored or buffered air. When the ophthalmic surgeon starts the docking procedure, a valve of the reservoir 220-4 or a connecting decondenser-hose 222 can be opened and the high pressure/low humidity/high temperature air can be directed from the reservoir 220-4 to the contact lens 216, greatly reducing and possibly eliminating the condensation on it. Numerous other combinations of the elements 220-1 to 220-6 can be used as well.

Figure 4A:
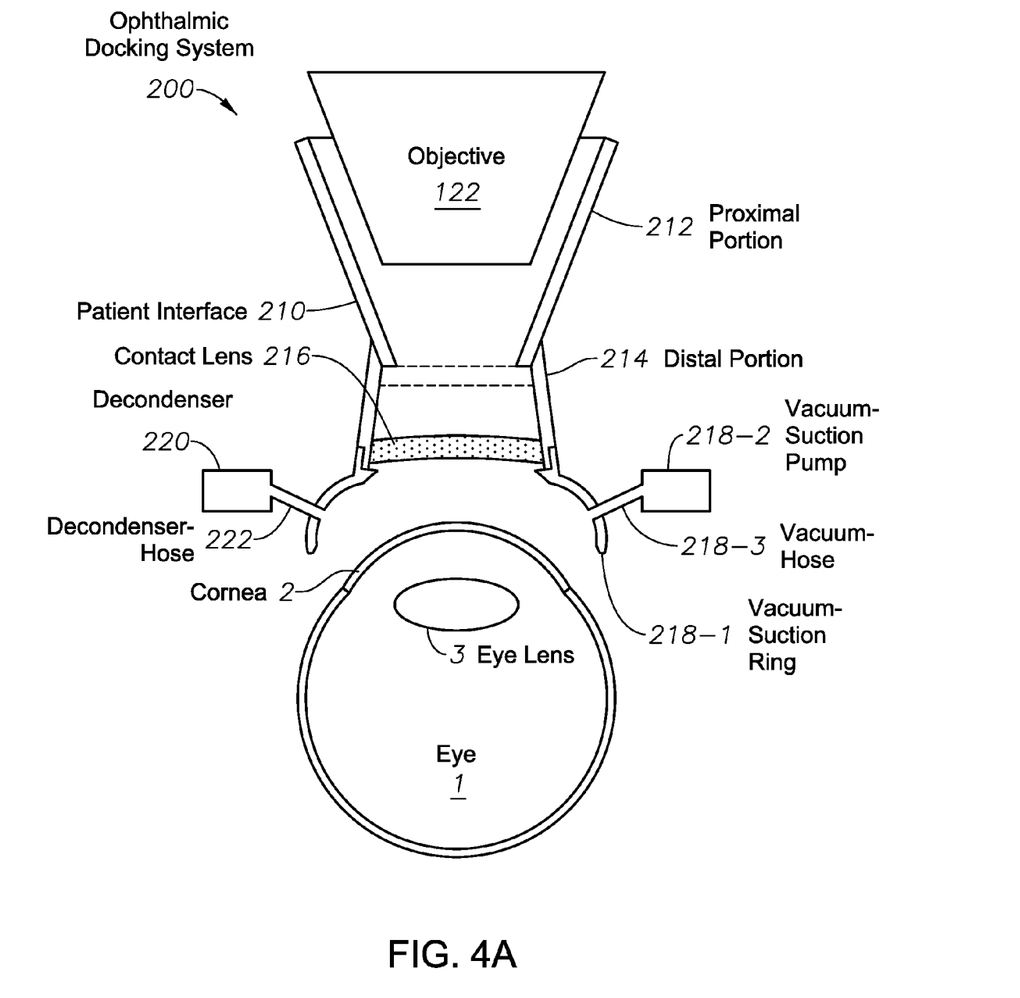
FIGS. 4A-F illustrate various embodiments of an ophthalmic docking system with a decondenser.

FIG. 4A illustrates that the interface attachment system 218 can include a vacuum-suction ring 218-1 that partially defines a toroidal volume when attached to the eye 1. The interface attachment system 218 can also include a vacuum-suction pump 218-2 that can generate vacuum suction, and a vacuum-hose 218-3 that can couple the vacuum-suction pump 218-2 to the vacuum-suction ring 218-1 to transfer the vacuum suction generated by the vacuum-suction pump 218-2 to the toroidal volume of the vacuum-suction ring 218-1 to create a seal between the vacuum-suction ring 218-1 and the eye 1, thereby attaching the patient interface 210 to the eye 1.

In other embodiments, the interface attachment system 218 can include a vacuum skirt, multiple vacuum-suction rings, or a vacuum-skirt with multiple flanges or ridges. When the vacuum-suction pump 218-2 applies a vacuum suction and this suction gets transferred by the vacuum-hose 218-3, these embodiments also get sealed to the eye 1 to provide an attachment or grip of the patient interface 210 to the eye 1.

The decondenser 220 can be coupled to the vacuum-suction ring 218-1 via a decondenser-hose, or decondenser-tubing 222. This decondenser-hose 222 can provide fluid communication between the decondenser 220 and the vacuum-suction ring 218-1.

In the embodiments of the decondenser 220 that defog the contact lens 216 by generating a suitable airflow, a coordinated regulation of the system can be used as the decondenser 220 may blow air into a chamber, defined by the contact lens 216 and the vacuum suction ring 218-1, whereas the vacuum-suction pump 218-2 removes air from the same chamber to create an attachment seal by vacuum suction. Because of these functions are opposing, a coordination of these two functions may be necessary to avoid the decondenser 220 working against the vacuum-suction pump 218-2. For example, while the objective 122 of the optic 120 is being aligned with the eye 1, the decondenser 220 can be operated whereas the vacuum-suction pump 218-2 may not be engaged. Once the patient interface 210 is lowered onto the eye 1 and the contact lens 216 makes contact with the eye 1, the decondenser 220 may stop and the vacuum-suction pump 218-2 may start to operate to create the attachment seal between the contact lens 216 and the eye 1.

Besides such embodiments needing a coordinated regulation, the surgical space around the patient interface 210 can be quite crowded. Thus, having two separate hoses or tubings 218-3 and 222 attached to the vacuum-suction ring 218-1 may pose challenges for managing the tight surgical space and access.

Figure 4B:
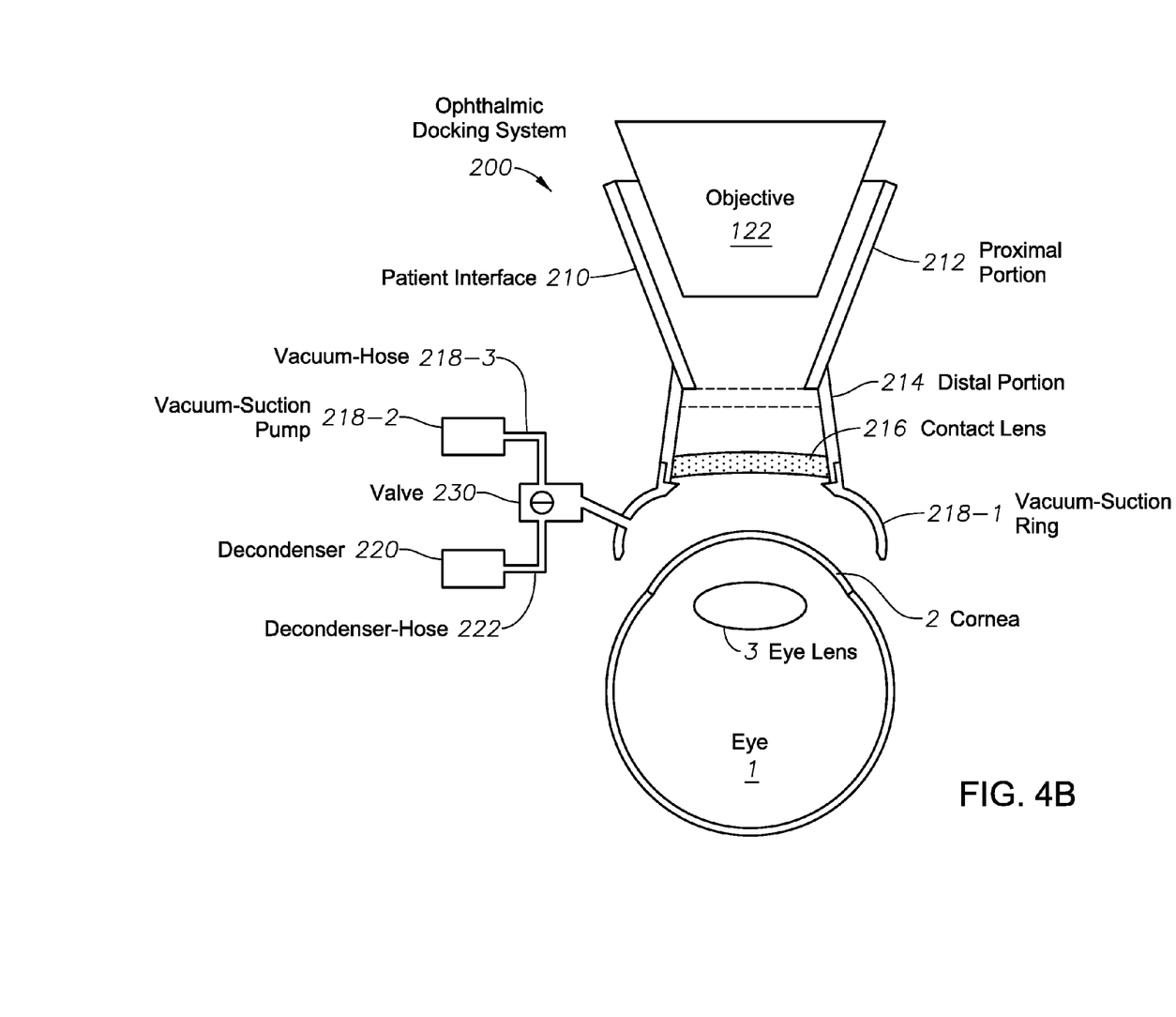

FIG. 4B illustrates an embodiment where the interface attachment system 218 and the decondenser system 220 are regulated or coordinated efficiently, as well as also reducing the clutter of the tight surgical space. The interface attachment system 218 may include the vacuum-suction ring 218-1 that can have a fluid coupling to a valve 230. The valve 230 can be coupled to the vacuum-suction pump 218-2 by the vacuum-hose 218-3 and to the desiccator 220 by the decondenser-hose 222.

The valve 230 can be capable of switching between a fluid communication channel connecting the vacuum-pump 218-2 and the vacuum-suction ring 218-1 and a fluid communication channel connecting the decondenser 220 and the vacuum-suction ring 218-1. With this architecture, the valve 230 can coordinate an operation of the vacuum-pump 218-2 with an operation of the decondenser 220 by granting fluid communication for only one of them to the vacuum-suction ring 218-1, thereby preventing that these two systems work against each other.

For example, during the alignment process of a docking procedure, the valve 230 may direct the heated or pressurized or dehumidified airflow from the decondenser 220 onto the contact lens 216 to keep the contact lens 216 condensation free, thus securing the high precision of the alignment. When the PI 210 is finally aligned with the center of the eye 1, or its lens 3, and the PI 210 is lowered towards the eye 1 docking with it, the valve 230 can switch fluid communication channels, disconnecting the decondenser 220 and connecting the vacuum-suction pump 218-2 to the vacuum-suction ring 218-1 to provide the vacuum-suction to complete the attachment of the patient interface 210 to the eye.

Embodiments with the valve 230 (i) can coordinate the operation of the decondenser 220 and the vacuum-suction pump 218-2 efficiently, (ii) can ensure that the contact lens 216 is kept condensation free up to the moment of the docking, and (iii) do not introduce additional space demands to the already crowded surgical space around the eye, such as the need for a second access port.

Figure 4C:
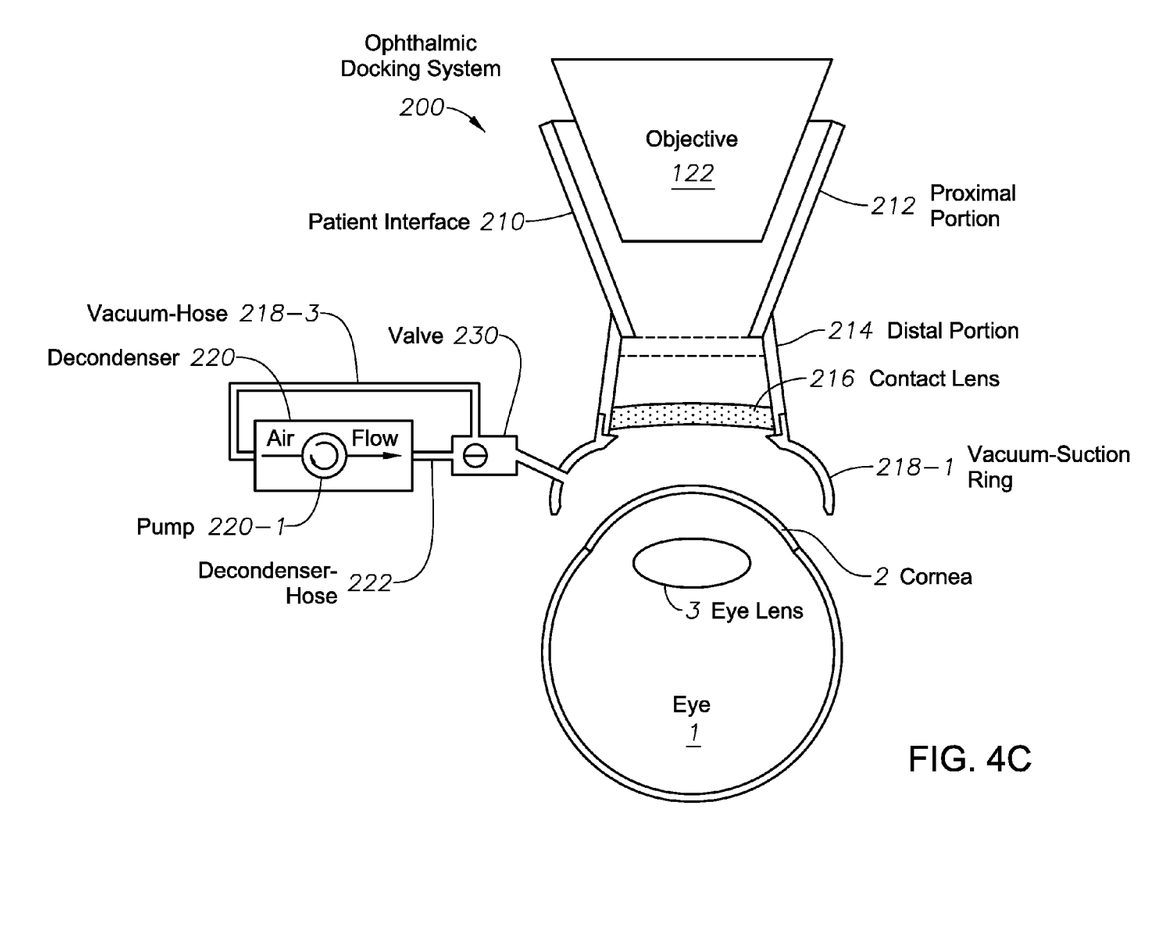

FIG. 4C illustrates an embodiment of the decondenser 220 that integrates the decondensing and vacuum-suction functionalities. The decondenser 220 can include the air pump 220-1 and either be coupled to the valve 230, or include the valve 230. The valve 230 can couple the vacuum-suction ring 218-1 to an input port of the pump 220-1 through the vacuum-hose 218-3, thereby transmitting the vacuum-suction created by the pump 220-1 to the vacuum-suction ring 218-1, or to an output port of the pump 220-1 through the decondenser hose 222, thereby applying the high pressure air outputted by the pump 220-1 to the vacuum-suction ring 218-1. In the alignment phase of the docking, the valve 230 may form the latter coupling to apply the high pressure or pumped air to the contact lens 216, switching to the former coupling to apply the vacuum-suction only when the vacuum-suction ring 218-1 actually makes contact with the eye.

Figure 4D:
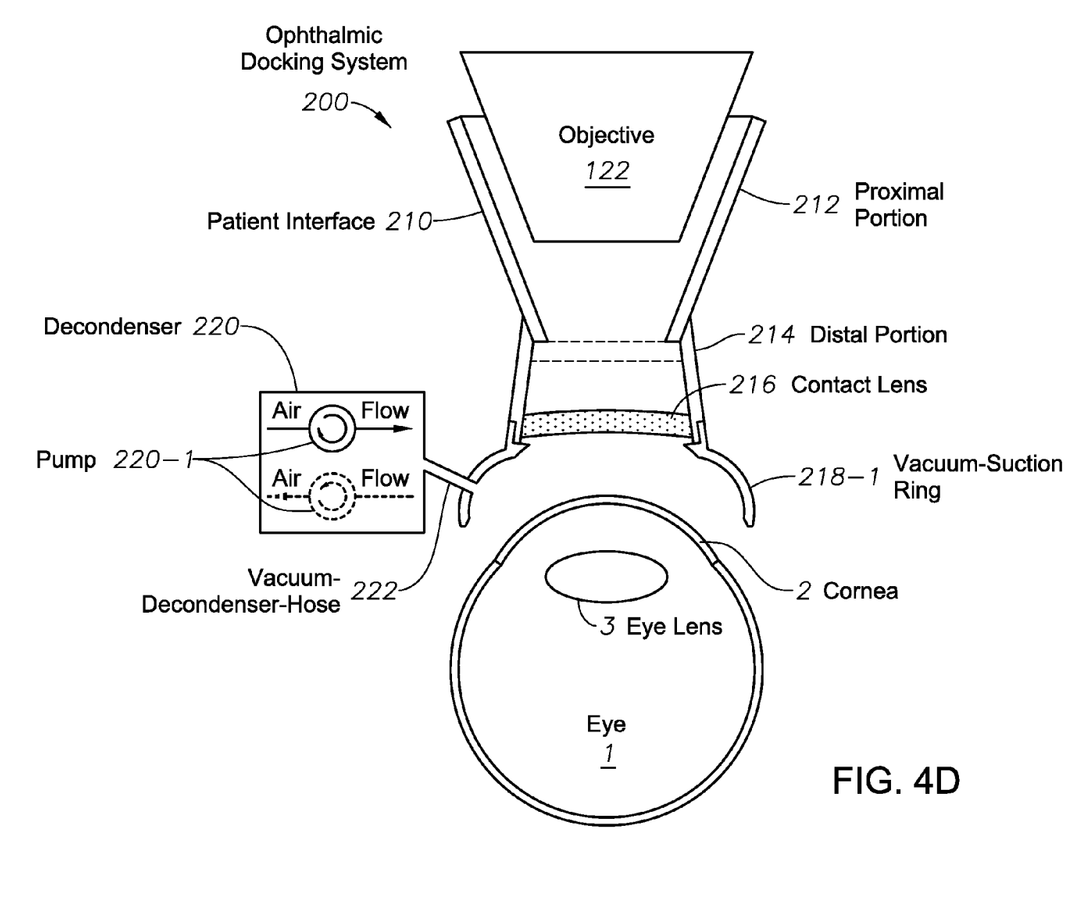

FIG. 4D illustrates another embodiment of the integrated decondenser 220 that includes the pump 220-1. In a first mode of operation, the decondenser 220 can run the pump 220-1 in one direction, making it work as an embodiment of the air pump 220-1 that applies high pressure air for the contact lens 216. In a second mode of operation, the decondenser 220 can run the pump 220-1 in a second direction, making it work as an embodiment of the vacuum-suction pump 218-2 that applies a vacuum suction to the vacuum-suction ring 218-1. In some embodiments the second direction can be a reverse of the first direction, corresponding to a clockwise and a counter-clockwise motion of a motor of the pump 220-1, thereby reversing a direction of the air flow, as shown with dashed lines.

Figure 4E:
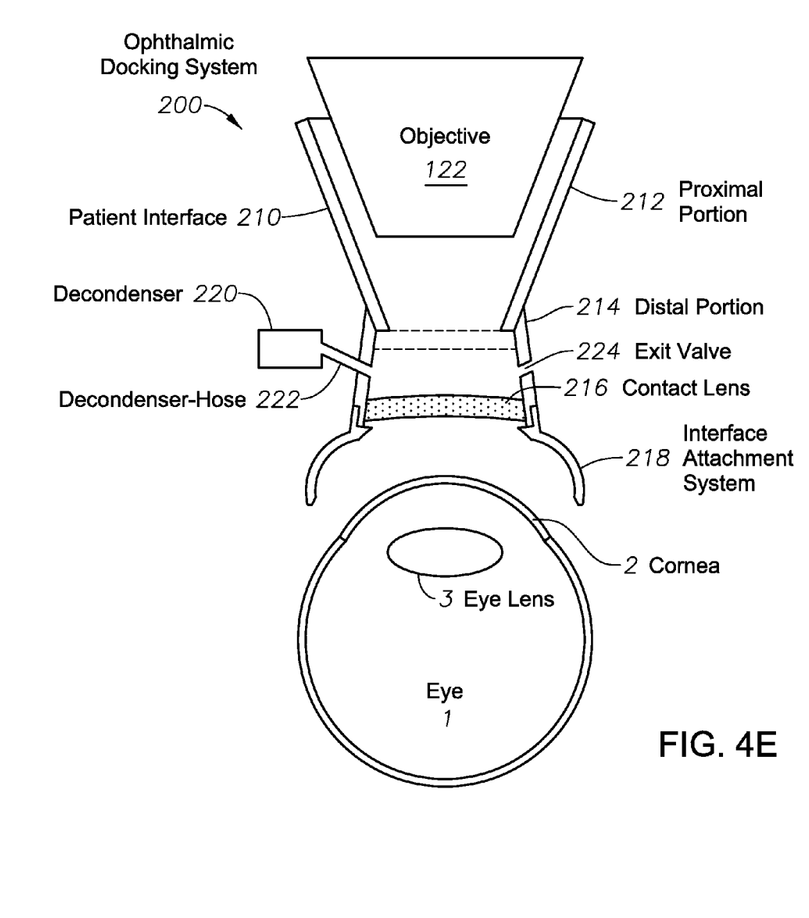
Figure 4F:
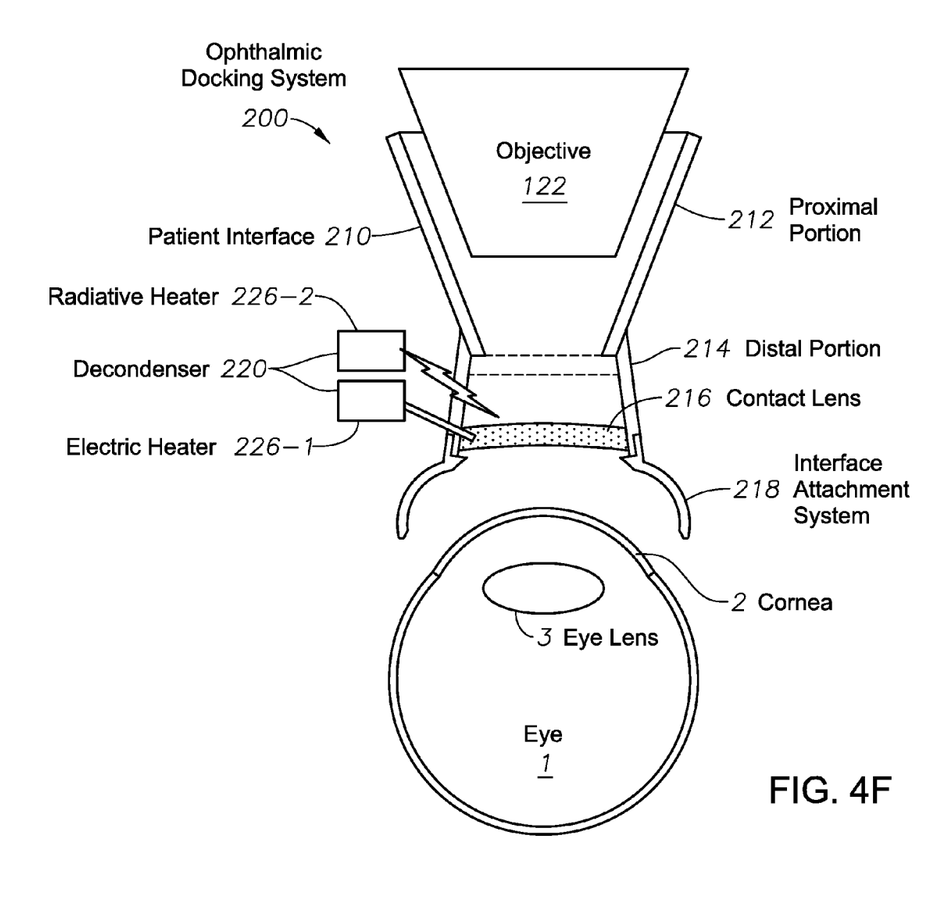

FIGS. 4E-F illustrate embodiments that do not apply an airflow directly to the eye. FIG. 4E illustrates an embodiment where the decondenser 220 is coupled to the patient interface 210 to provide an airflow to the contact lens 216 on its non-contact side where the contact lens 216 is not configured to be in direct contact with the eye. In this embodiment it is possible to continue heating the contact lens 216 even after docking.

FIG. 4F illustrates an embodiment where the heating of the contact lens is performed without applying an airflow. In such an embodiment the decondenser 220 can include, for example, an electric heater 226-1 to increase or manage the temperature of the contact lens 216. Other embodiments of the decondenser 220 can apply radiative heating, e.g. by including an infrared source as a radiative heater 226-2 radiating an infrared beam onto the contact lens 216 to reduce condensation on the contact lens 216.

The embodiments of FIGS. 4E-F that do not apply an airflow to the eye avoid drying the eye, thereby reducing the chance of corneal abrasions. Distortions of the optic 120 by the heating can be avoided or minimized if the optic 120 is designed for a temperature around the body temperature, such as 37 C, or for a heating temperature.

Figure 5:
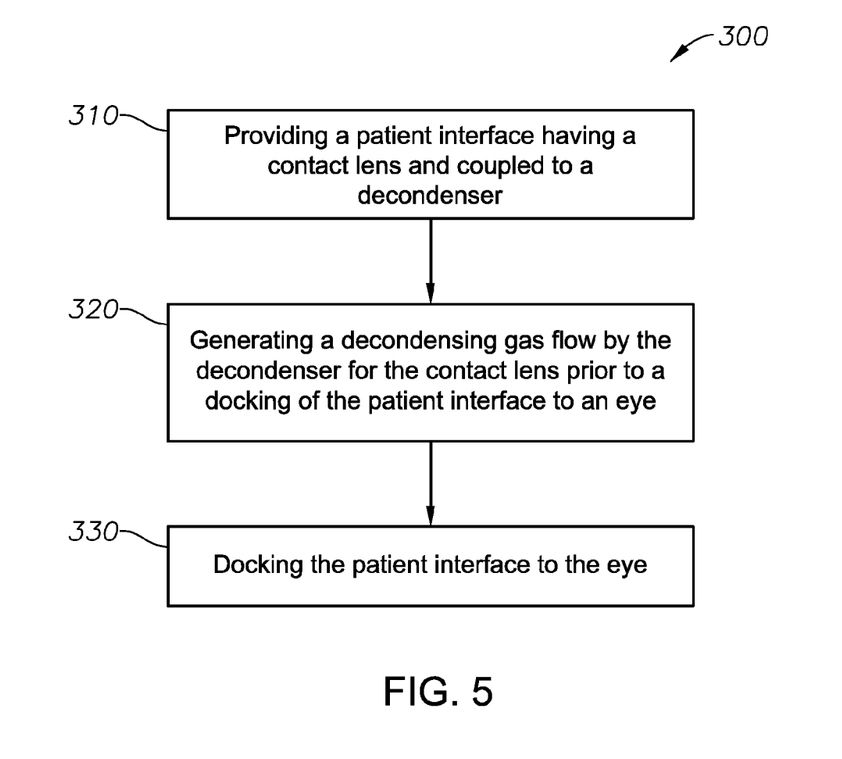
FIG. 5 illustrates a method of ophthalmic docking with a decondenser.

FIG. 5 illustrates a method 300 of operating the ophthalmic docking system 200. The method of ophthalmic docking 300 can include: a providing 310 of a patient interface having a contact lens and coupled to a decondenser; a generating 320 of a decondensing gas flow by the decondenser for the contact lens prior to a docking of the patient interface to an eye; and a docking 330 of the patient interface to the eye. Here the patient interface can be the PI 210, the contact lens can be the contact lens 216, and the decondenser can be the decondenser 220.

In some embodiments, the generating 320 can include generating a heated airflow by an air pump and an air heater, such as the air pump 220-1 and the air heater 220-3. In some embodiments, the generating 320 can include generating a dehumidified airflow by the air pump 220-1 and a dehumidifier, such as the dehumidifier 220-2. In some embodiments, the generating 320 can include generating a pressure-regulated airflow by the air pump 220-1, the reservoir 220-4 and possibly by the pressure regulator 220-5.

Figure 6:
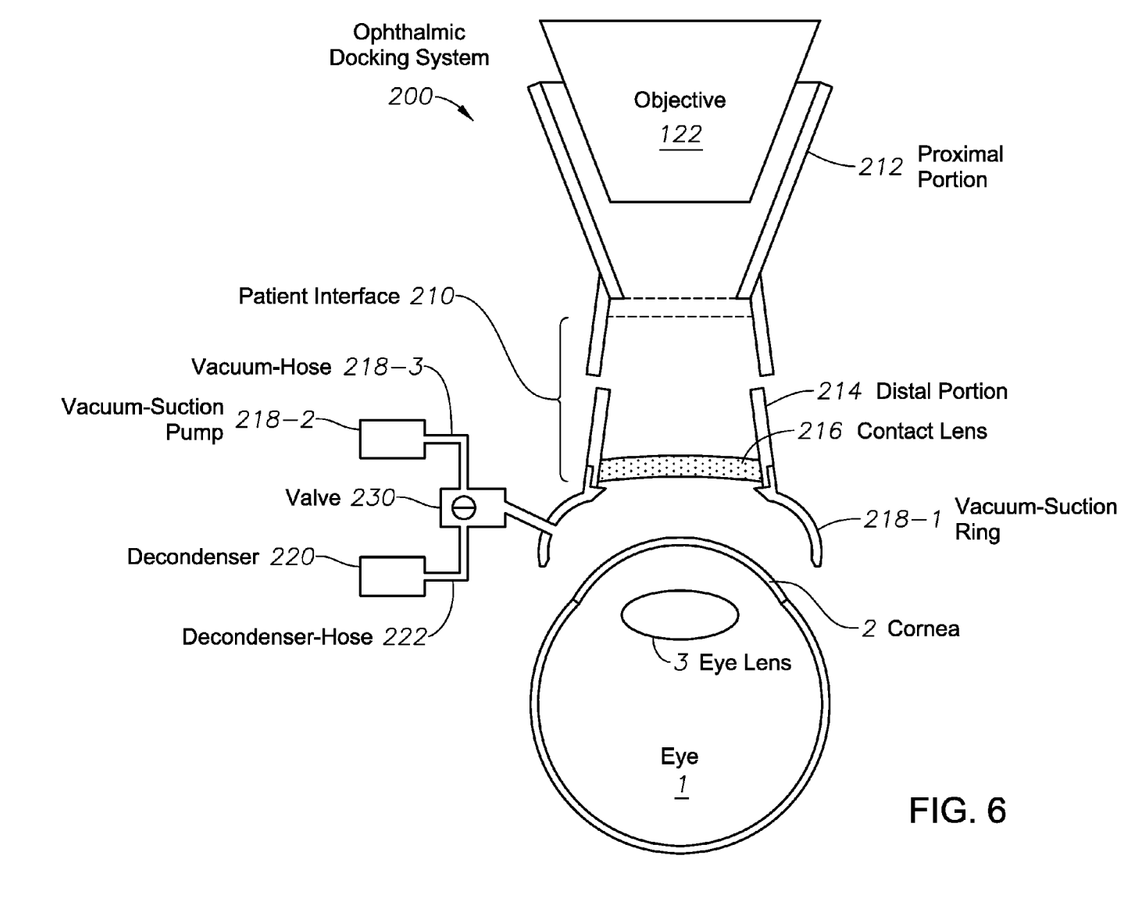
FIG. 6 illustrates an ophthalmic docking system with a two-piece patient interface.

FIG. 6 illustrates that some embodiments of the ophthalmic docking system 200 can include a patient interface 210 where the proximal portion 212 and the distal portion 214 are separate elements. The distal portion 214 can be coupled to the elements 216-230 of the embodiment of FIG. 4B, including the valve 230, the decondenser 220, and the vacuum-suction pump 218-1. An advantage of such two-piece PIs is that the distal portion 214 may be more easily aligned and docked with the eye than the one-piece PIs, since the alignment does not require the adjustment of the objective 122 of the optic 120 by the gantry 152.

On the other hand, in such two-piece PIs the proximal portion 212 and the distal portion 214 needs to be coupled together after the distal portion 214 has been attached to the eye. Therefore, the coupling is typically performed by the surgeon and not as part of the manufacturing process. This in-situ coupling can possibly lead to imprecision of the alignment of the distal portion 214 and especially its contact lens 216 with the optic 120 of the laser system 100. To offer improved precision and ease of this coupling process, some embodiments can include a grip system to mechanically maneuver the distal portion 214 more precisely during the alignment and the coupling.

Figure 7:
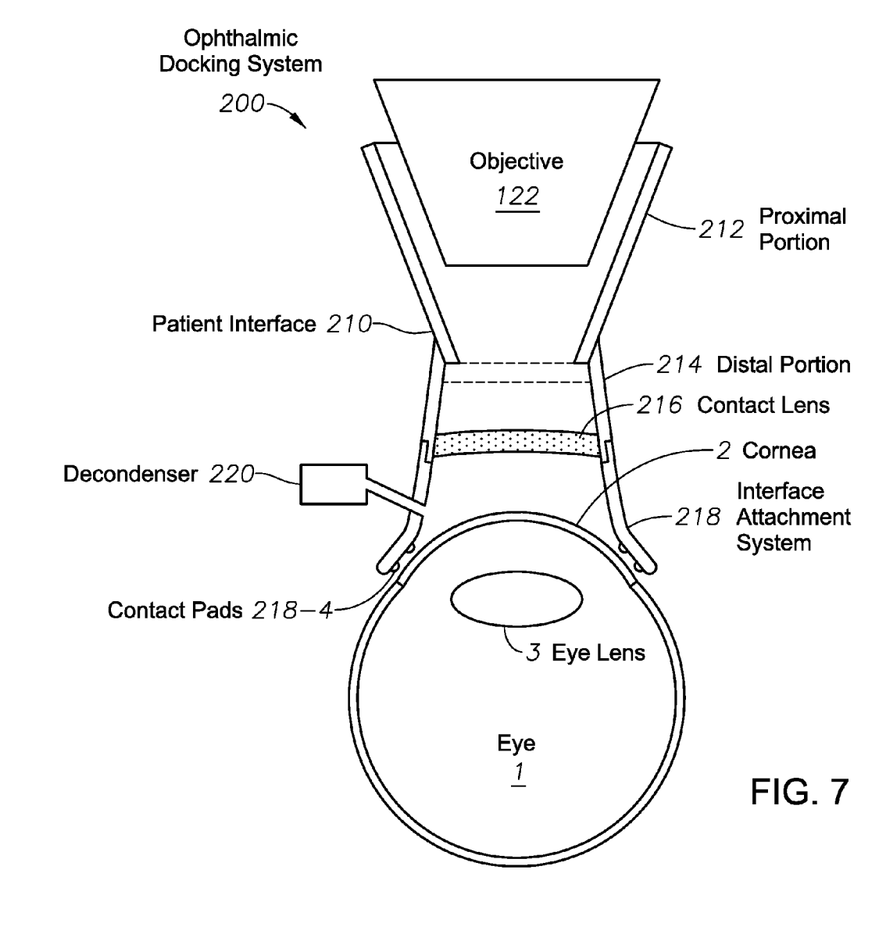
FIG. 7 illustrates a patient interface where the attachment system includes contact pads.

FIG. 7 illustrates another embodiment of the ophthalmic docking or interface system 200 that can include the patient interface 210, attachable to the ophthalmic surgical laser system 100 through its objective 122. The PI 210 can include the contact lens 216 to be docked to the eye 1. The interface system 200 can further include a desiccating or decondenser system 220 that can direct a desiccating gas flow to a chamber formed at the contact lens 216.

Embodiments of the patient interface 210 can include an interface attachment system 218 that includes a set of contact pads 218-4. These contact pads 218-4 concentrate the force pressing the PI 210 to the eye 1 onto small areas, thus increasing the pressure. The increased pressure can press the contact pads 218-4 deep into a corneal tissue, thus making the attachment of the PI 210 to the eye 1 firm. Such embodiments can be simple as they attach the PI 210 to the eye only by the mechanical pressure of the contact pads 218-4 instead of vacuum suction systems.

In other embodiments, the PI 210 can include the vacuum-suction ring 218-1 to facilitate the attachment of the PI 210 to the eye 1, and the ophthalmic interface system 200 can include the vacuum-suction pump 218-2 to provide vacuum suction. In these embodiments the desiccating gas of the desiccator 220 and the vacuum suction of the vacuum-suction pump 218-2 can be provided through the same hose or tubing to the patient interface 210.

While this specification contains many specifics, these should not be construed as limitations on the scope of the invention or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

What is claimed is:

1. An ophthalmic docking system, comprising:
   a patient interface, having
      a proximal portion configured to be attached to an ophthalmic system,
      a distal portion configured to be attached to an eye, comprising
         a contact lens, and
         an interface attachment system;
   a decondenser, coupled to the patient interface and configured to reduce a vapor condensation on the contact lens;
   a vacuum-suction ring, configured to form a sealable coupling when attached to the eye; and
   a vacuum-hose, configured to couple a vacuum-suction pump and the vacuum-suction ring to transfer a vacuum suction, generated by the vacuum-suction pump, to the vacuum-suction ring to create the sealed coupling between the vacuum-suction ring and the eye, thereby attaching the patient interface to the eye.

2. The ophthalmic docking system of claim 1, the decondenser comprising:
   an air pump, configured to pump air towards the interface attachment system.

3. The ophthalmic docking system of claim 2, the decondenser comprising:
   at least one of a gas container and a reservoir, configured
      to store high-pressure air pumped by the air pump at a pressure higher than an ambient pressure, and
      to forward the high-pressure air towards the interface attachment system.

4. The ophthalmic docking system of claim 3, the decondenser comprising:
   a pressure-regulator, coupled to the reservoir and configured to forward the high-pressure air towards the interface attachment system with a pressure fluctuation smaller than a pressure fluctuation of the high-pressure air pumped by the air pump to the reservoir.

5. The ophthalmic docking system of claim 1, the decondenser comprising:
   a dehumidifier, configured to reduce a vapor content of an airflow directed towards the interface attachment system.

6. The ophthalmic docking system of claim 1, the decondenser comprising:
   an air-heater, configured to increase a temperature of an airflow directed towards the interface attachment system.

7. The ophthalmic docking system of claim 1, wherein:
   the decondenser is coupled to the vacuum-suction ring via a decondenser-hose.

8. The ophthalmic docking system of claim 1, wherein:
   the ophthalmic docking system comprises a valve, coupled to the vacuum-suction ring; and
   the vacuum-hose and the decondenser-hose are coupled to the vacuum-suction ring through the valve, wherein the valve is capable of switching between a first fluid communication channel coupling the vacuum-pump and the vacuum-suction ring and a second fluid communication channel coupling the decondenser and the vacuum-suction ring.

9. The ophthalmic docking system of claim 1, wherein:
   the interface attachment system comprises a vacuum-suction ring;
   the ophthalmic docking system comprises a valve, coupled to the vacuum-suction ring and the decondenser; and
   the decondenser comprises an air pump, wherein
   the valve is capable of switching between a first fluid communication channel coupling an air-intake port of the air pump and the vacuum-suction ring, and a second fluid communication channel coupling an air-output port of the air pump and the vacuum-suction ring.

10. The ophthalmic docking system of claim 1, wherein:
    the interface attachment system comprises a vacuum-suction ring, configured to partially define a toroidal volume when attached to the eye; and
    the decondenser comprises an air pump, coupled to the vacuum-suction ring by a vacuum-decondenser-hose, wherein
    an operation of the air pump can be switched between a first mode to apply pumped air for the contact lens through the vacuum-decondenser-hose, and a second mode to apply vacuum suction to the vacuum-suction ring through the vacuum-decondenser-hose.

11. The ophthalmic docking system of claim 1, wherein:
    the decondenser is configured to heat the contact lens on a side that does not contact the eye.

12. The ophthalmic docking system of claim 1, the decondenser comprising:
    an electric heater or a radiative heater.

13. The ophthalmic docking system of claim 1, wherein:
    the proximal portion and the distal portion are separate elements; and
    the proximal portion and the distal portion can be coupled together after the distal portion has been attached to the eye.

14. The ophthalmic docking system of claim 1, the distal portion comprising:
    a grip system, configured to assist the mechanical fastening of the patient interface to the eye.

* * * * *